(12) United States Patent
Lenselink et al.

(10) Patent No.: US 6,319,889 B1
(45) Date of Patent: Nov. 20, 2001

(54) CHEMICAL COMPOUNDS AND PERFUME COMPOSITION

(75) Inventors: Willem Lenselink, Voorthuizen; Anton Pieter Johan van Manen, Putten, both of (NL)

(73) Assignee: PFW Aroma Chemicals B.V. (NL)

( * ) Notice: Subject to any disclaimer, the term of this patent is extended or adjusted under 35 U.S.C. 154(b) by 0 days.

(21) Appl. No.: 09/360,306

(22) Filed: Jul. 23, 1999

(51) Int. Cl.⁷ ............................................. A61K 7/46
(52) U.S. Cl. .................. 512/8; 512/20; 512/22; 512/23; 512/25; 568/659; 568/664
(58) Field of Search .................. 568/659, 664; 512/8, 20, 22, 23, 25

(56) References Cited

U.S. PATENT DOCUMENTS

| | | | |
|---|---|---|---|
| 4,357,319 | * 11/1982 | Sprecker | 424/84 |
| 4,362,657 | * 12/1982 | Kiwala et al. | 512/20 |
| 4,554,096 | * 11/1985 | Wiegers et al. | 512/20 |

* cited by examiner

*Primary Examiner*—Jill Warden
*Assistant Examiner*—Monique T. Cole
(74) *Attorney, Agent, or Firm*—Hoffmann & Baron, LLP

(57) ABSTRACT

The invention is directed to novel compounds selected from the class of compounds having the structural formulae

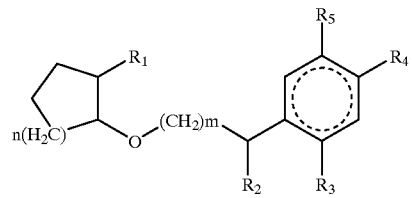

wherein the cyclohexane moiety with the dotted circle represents either a cyclohexane ring or a benzene ring, n represents an integer with the value 1, 3, or 4, m represents an integer with the value 1 or 2, $R_1$, $R_2$, $R_3$, $R_4$ and $R_5$, represent hydrogen or a lower alkyl group, and the total carbon number of $R_1$, $R_2$, $R_3$, $R_4$ and $R_5$, combined is eight or less.

24 Claims, No Drawings

CHEMICAL COMPOUNDS AND PERFUME COMPOSITION

This invention relates to new chemical compounds useful as perfumes or as components of perfumes. More specifically it relates to ethers comprising a cycloalkyl moiety combined with either a phenylalkyl or a cyclohexylalkyl moiety.

There is a continuing search for materials having useful perfumery fragrance characteristics. These materials are sought either as replacements for naturally occurring compounds or as totally new scents or odour notes in their own right. For practicability reasons such materials should possess other favorable properties e.g. stability in applications and human and environmentally safety, all in addition to their useful odour notes.

It is the object of the present invention to provide a series of novel and practicable synthetic materials, being ethers comprising a cycloalkyl moiety combined with either a phenylalkyl or a cyclohexylalkyl moiety, and possessing very useful odours of the floral type. These novel ethers are represented by the generic formula I

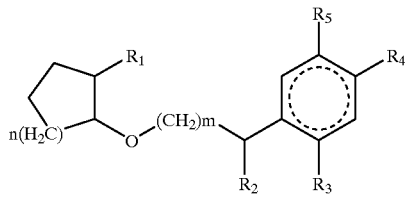

wherein the cyclohexane moiety with the dotted circle represents either a cyclohexane ring or a benzene ring, n represents an integer with the value 1, 3, or 4, m represents an integer with the value 1 or 2, $R_1$, $R_2$, $R_3$, $R_4$ and $R_5$ represent hydrogen or a lower alkyl group, and the total carbon number of $R_1$, $R_2$, $R_3$, $R_4$ and $R_5$ combined is eight or less.

In the present context the term 'lower alkyl' indicates a straight or branched alkyl group of 1–6 carbon atoms.

It will be apparent that the novel ethers can exist in a variety of positional, stereoisomeric and enantiomeric forms and it is intended that these be included within the structural formulae.

According to a preferred embodiment n represents the value 1. More preferred is the situation wherein n and m both represent the value 1.

As indicated above the cyclohexane moiety with the dotted circle represents either a benzene ring or a saturated ring. In a preferred embodiment the cyclohexane moiety with the dotted circle is a benzene ring.

In the invention $R_1$, $R_2$, $R_3$, $R_4$ and $R_5$ represent hydrogen or a lower alkyl, as defined herein. In a preferred embodiment $R_1$, $R_2$, $R_3$, $R_4$ and $R_5$, represent hydrogen. In an alternative embodiment $R_1$ and $R_2$ are each selected from hydrogen, methyl and ethyl, and $R_3$, $R_4$ and $R_5$ are each selected from hydrogen and straight and branched alkyl groups comprising from 1 to 6 carbon atoms.

According to a specially preferred embodiment the compounds of the invention may be used in combination with a compound selected from the class of compounds having the structural formulae

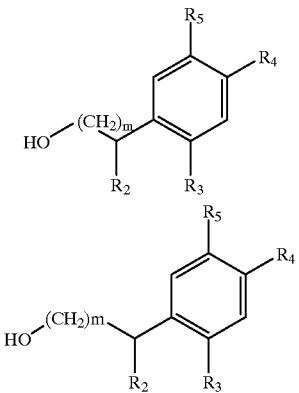

wherein m represents an integer with the value 1 or 2 and $R_2$, $R_3$, $R_4$ and $R_5$, represent hydrogen or a lower alkyl group, and/or with a compound selected from the class of compounds having the structural formulae

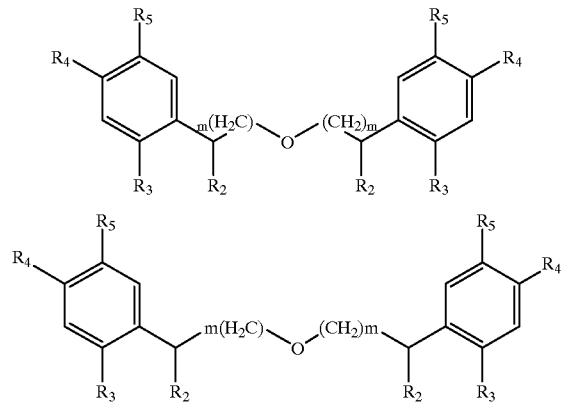

wherein m represents an integer with the value 1 or 2 and $R_2$, $R_3$, $R_4$ and $R_5$, represent hydrogen or a lower alkyl group, provided that the compounds of that mixture have the same definition for m, $R_2$, $R_3$, $R_4$ and $R_5$.

Fragrance chemicals containing cycloalkyl, phenylalkyl or cyclohexylalkyl moieties are well known in perfumery. Many of them are subject of a monograph in "Perfume and Flavor Chemicals" by S. Arctander (published by the author, 1969). The major part of them belong to the chemical class of alcohols and the corresponding esters. One of the most widely used of all perfume chemicals is phenylethyl alcohol, mainly to impart a rosy odour effect. Also ethers of phenylethyl alcohol are known. Arctander describes respectively the methyl, ethyl, propyl, i-amyl, heptyl, benzyl, tetrahydropyranyl and vinyl ether of phenylethyl alcohol. $C_3$ and $C_6$ secondary alkyl and $C_4$ alkenyl ethers of phenylethyl alcohol are disclosed in the U.S. Pat. Nos. 4,328,206 and 4,357,319 and in European patent 49120. The 2-methyl-2-butenyl ether of phenylethyl alcohol is disclosed in French patent 2373276. Ethers of cyclohexyl alcohols and phenylethyl alcohols are described in the U.S. Pat. No. 4,306,096, 4,324,923, 4,335,008, 4,337,180, 4,343,791, 4,346,080, 4,350,733, 4,362,657, 4,371,715, 4,374,746 and in European patent 49120, Polyurethane foams containing ethers of cyclohexyl alcohols and phenylethyl alcohols are disclosed in U.S. Pat. 5,436,276 and British patent 2283750. Polymer compositions containing ethers of cyclohexyl alcohols and phenylethyl alcohols are disclosed in Canadian patent 2051469.

The novel ethers of the invention can be prepared by methods known in the art for analogous compounds. Overviews may be found in, inter alia, J. March, Advanced Organic Chemistry Reactions, Mechanisms, and Structure, 4$^{th}$ edition, J. Wiley & Sons, New York, 1992, Appendix C, Ethers, pp. 1285–1286, and R.C. Larock, Comprehensive Organic Transformations, A Guide to Functional Group Preparations, VCH Publishers, Inc., New York, 1998, Ethers, pp. 439–473. Of the many general methods known for ether formation, the preferred method for each compound may be different and will depend on considerations of economics, availability of starting materials, by-product formation, technical feasibility, safety, organoleptic grade produced, and the like, which parameters, circumstances and conditions may be subject to change over time, location, facility etc.

Generally preferred chemical methods in this context are dehydration of alcohols, addition of alcohols to alkenes and reaction between alkoxides and alkyl halides known to the art as Williamson synthesis. For the ethers of the invention the first two of these methods are especially preferred in terms of practicability and economics, i.e. the possibilities to avoid the use of solvents additional chemicals and waste streams, accessibility and economics of starting materials, simplicity of procedures, work up, purification, equipment, reaction conditions and the ease to arrive at organoleptically acceptable end products. It will be apparent that dehydration of two different alcohols may lead to three theoretically possible ethers, being the result of the combination of two identical alcohols and two different alcohols. Also, in the acid catalyzed addition of alcohols to alkenes, the dehydration of the alcohol involved can be a serious side reaction leading to the symmetrical ether from two identical alcohol molecules as a by-product. In the above referred to patent literature similar methods are described for ethers with a cyclohexyl and phenylethyl moiety. In the East German patent 289262 the two step preparation of mixed phenylethyl ethers from alcohols and phenyloxirane is disclosed. Ruthenium complex catalyzed addition of phenylethyl alcohol to alkenes is disclosed in J. Organomet. Chem (1995), 489 (1–2), 83–91.

The novel ethers of the invention exhibit a variety of useful odour nuances with natural green/ stemmy, leafy-floral and a honey-sweet character, reminiscent of hyacinth and sweet pea, unexpectedly out performing the ethers with phenylethyl moieties known to the art in terms of natural floralness, radiance and odour substantivity, which makes them specially suitable to be applied in fabric care, functional care and personal care consumer products. They can be used as fragrances per se or as components of a fragrance composition.

The invention is also directed to a "fragrance composition" or perfume composition comprising at least one compound according to the invention, preferably in combination with other olfactory active ingredients.

The term "fragrance composition" is used to denote a mixture of compounds including, for example, natural oils, synthetic oils, alcohols, aldehydes, ketone, esters, lactone, ethers, hydrocarbons, nitriles and other classes of chemical compounds which are admixed so that the combined odours of the individual components produce a pleasant or desired fragrance. Such fragrance compositions or the novel compounds of the invention alone can be used in conjunction with carriers, vehicles or solvents containing also as needed, dispersants, emulsifiers, surface-active agents, aerosols propellants odour release influencing agents and the like. In fragrance compositions the individual components contribute their particular olfactory characteristics, but the overall effect of the composition is the sum of the effect of each ingredient. Thus, the compounds of the invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of the compounds of the invention which will be effective in the final composition, depends on many factors including the characteristics of the other ingredients, their amounts and the effects which are desired. It has been found that as little as 0.001% by weight of compounds of this invention can be used to alter the effect of a fragrance composition.

The amount employed will depend on considerations of cost, nature of end product, the effect desired in the finished product, and the particular fragrance sought, but will usually not be more than about 40% by weight. The compounds disclosed herein can be used in a wide variety of applications, by way of example but not limited thereto, detergents and soaps, air fresheners, perfumes, colognes, after shave lotions, preparations such as bath oils and bath salts, hair preparations such as lacquers, brilliantines, pomades and shampoos, cosmetic preparations such as creams, deodorants, hand lotions and sun screens, powders such as talcs, dusting powders, face powders, masking agents, household products such as bleaches, cleaners and in technical products such as shoe polish and automobile wax.

The invention is further directed to these end products containing an amount of the compounds according to the invention.

The following examples illustrate the invention without limitation thereto.

EXAMPLE 1

A mixture of 175 g phenylethyl alcohol, 155 g cyclopentanol and 37 g 96% sulphuric acid was heated to 100–109° C. with stirring and removal of the water formed (22 g) by means of a Dean-Stark trap for 4.5 hrs. To the reaction mixture was added at room temperature 200 ml pentane. The lower layer was washed three times with 200 ml pentane and once with 100 ml pentane. The combined pentane layers were washed with 200 ml 5% aqueous sodium bicarbonate solution, dried over sodium sulphate and concentrated on a rotatory evaporator, leaving 70 g of a mixture containing 8% phenylethyl alcohol, 85% phenylethyl cyclopentyl ether and 2% diphenylethyl ether by GC analysis, which was vacuum distilled. The fraction with a boiling range of 63–78° C. at 0.9 mbar (57 g, phenylethyl cyclopentyl ether content 98.9% by GC analysis) was subjected to flash column chromatography over silica with a 1:10 diethyl ether/pentane mixture, yielding 47 g phenylethyl cyclopentyl ether of 99.9% purity by GC analysis, $n_D^{20}$=1.5099.

EXAMPLE 2

A mixture of 75 g phenylethyl alcohol and 4 g AMBERLYST® 15 was heated to 100° C. with stirring. 20 g cyclopentene was added over a period of 3.5 hrs and the mixture was heated for 2 more hours at 103–110° C. The filtrated reaction mixture (92 g, containing 5%

Cyclopentene, 45% phenylethyl alcohol, 27% of phenylethyl cyclopentyl ether and 5% diphenylethyl ether by GC analysis) was subjected to fractional distillation. The fraction boiling at 70–73° C. at 0.85 mbar (25 g) consisted of phenylethyl cyclopentyl ether of 99.8% purity, $n_D^{20}=1.5098$.

EXAMPLE 3

A mixture of 183 g phenylethyl alcohol, 980 g cyclohexane and 14 g AMBERLYST® 15 was heated to reflux (83° C.) with stirring. cyclooctene over a period of 3 hrs. After refluxing for 13 hrs at 83–89° C. the mixture was filtrated and concentrated on a rotatory evaporator at 45° C. and 25 mbar resulting in 233 g concentrate, containing 17% cyclooctene, 58% phenylethyl alcohol and 18% phenylethyl cyclooctyl ether and 2% diphenylethyl ether by GC analysis, which was vacuum distilled. The fraction with a boiling range of 89–103° C. at 0.7 mbar (13 g containing 7% phenylethyl alcohol, 80% phenylethyl cyclooctyl ether and 10% diphenylethyl ether by GC analysis) was subjected to flash column chromatography over silica with a 1:25 diethyl ether/pentane mixture, yielding 5 g phenylethyl cyclooctyl ether of 97.4% purity by GC analysis, $n_D^{20}=1.5175$.

EXAMPLE 4

Perfume compositions of the floral, magnolia type, especially suited for fabric care applications, such as detergents and fabric softeners, were prepared by admixing the following ingredients:

|  | Parts by weight |
| --- | --- |
| Adoxal (IFF), 10% in dipropylene glycol | 10 |
| Dihydroisojasmonate (PFW) | 15 |
| 12-Oxahexadecanolide (PFW) | 25 |
| Frutalone (PFW) | 25 |
| Heliotropin | 25 |
| Osmanthus Fleuriff (IFF) | 25 |
| Ylanga Base (PFW) | 25 |
| Guava Base (PFW) | 50 |
| Dipropylene glycol | 150 |
| Tilianol Super (PFW) | 150 |
| Melione Base (PFW) | 500 |
|  | 1000 |

B. The formulation above wherein the 150 parts by weight of dipropylene glycol is replaced by the same amount of the ether of Example 2.

The substitution of dipropylene glycol by the ether of Example 2 gives the fragrance surprisingly more floralness and naturalness, radiance and long lastingness, making it more desired and suitable for its purposes.

EXAMPLE 5

Perfume compositions of the floral, hyacinth type, especially suited for fine fragrances, eau de toilettes and cosmetic applications, were prepared by admixing the following ingredients:

| Geranium oil Bourbon | 5 |
| --- | --- |
| Neroli oil | 5 |
| Galbanum resinoid | 10 |
| Helional | 10 |
| Petit grain oil terpeneless | 10 |

-continued

| Coumarin extender (PFW) | 15 |
| --- | --- |
| Florazolone (IFF) | 15 |
| Heliotropin | 15 |
| Mandarin Isolate (PFW) | 20 |
| Rosessence (Firmenich) | 20 |
| Ylanga Base (PFW) | 20 |
| Calone, 10% in dipropylene glycol (CAL) | 25 |
| Dihydroisojasmonate (PFW) | 25 |
| Guava Base (PFW) | 25 |
| Melione Base (PFW) | 25 |
| Osmanthus Fleuriff (IFF) | 25 |
| Oxambrane, 10% in dipropylene glycol (PFW) | 25 |
| 12-Oxahexadecanolide (PFW) | 50 |
| Dipropylene glycol | 50 |
| Iso E Super (IFF) | 50 |
| Lemolate (PFW) | 50 |
| Jasmin Base (PFW) | 60 |
| Vertofix Coeur (IFF) | 70 |
| Bergamot oil | 75 |
| Linalyl acetate | 75 |
| Lyral (IFF) | 75 |
| Hedione (Firmenich) | 150 |
|  | 1000 |

B. The formulation A wherein the 50 parts by weight of dipropylene glycol is replaced by the same amount of the ether of Example 2.

The substitution of dipropylene glycol by the ether of Example 2 gives the fragrance surprisingly more floralness and naturalness and a rounding off effect which makes it more desired and useful for its application.

What is claimed is:

1. A compound selected from the class of compounds having the structural formulae

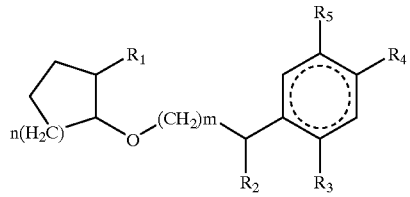

wherein the cyclohexane moiety with the dotted circle represents either a cyclohexane ring or a benzene ring, n represents an integer with the value 1, 3, or 4, m represents an integer with the value 1 or 2, $R_1$, $R_2$, $R_3$, $R_4$ and $R_5$, represent hydrogen or a lower alkyl group, and the total carbon number of $R_1$, $R_2$, $R_3$, $R_4$ and $R_5$ combined is eight or less.

2. A compound according to claim 1 wherein n represents the value 1.

3. A compound according to claim 1 wherein the cyclohexane moiety with the dotted circle represents a benzene ring.

4. A compound according to claim 3 wherein n and m both represent the value 1.

5. A compound according to claim 4 wherein $R_1$, $R_2$, $R_3$, $R_4$, and $R_5$, represent hydrogen.

6. A mixture of compounds comprising:

a) a compound selected from the class of compounds having the structural formulae

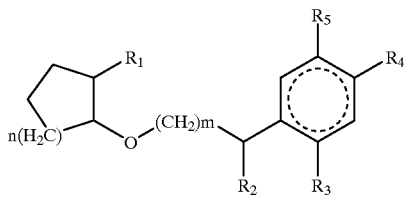

wherein the cyclohexane moiety with the dotted circle represents a benzene ring, n represents an integer with the value 1, 3, or 4, m represents an integer with the value 1 or 2, $R_1$, $R_2$, $R_3$, $R_4$, and $R_5$ represent hydrogen or a lower alkyl group, and the total carbon number of $R_1$, $R_2$, $R_3$, $R_4$, and $R_5$ combined is eight or less; and b) a compound selected from the class of compounds having the structural formulae

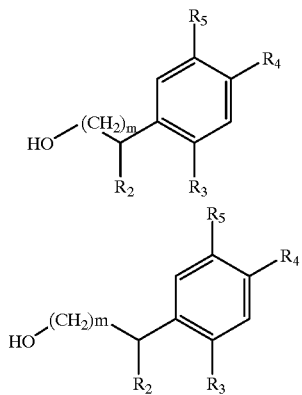

wherein m represents an integer with the value 1 or 2 and $R_2$, $R_3$, $R_4$, and $R_5$ represent hydrogen or a lower alkyl group, and/or with a compound selected from the class of compounds having the structural formulae

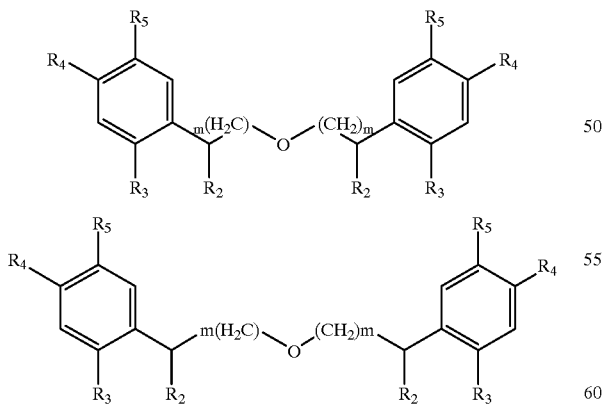

wherein m represents an integer with the value 1 or 2 and $R_2$, $R_3$, $R_4$, and $R_5$ represent hydrogen or a lower alkyl group, provided that the compounds of that mixture have the same definition for m, $R_2$, $R_3$, $R_4$, and $R_5$.

7. A compound according to claim 6 wherein n and m both represent the value 1.

8. A compound according to claim 6 wherein $R_1$, $R_2$, $R_3$, $R_4$, and $R_5$ represent hydrogen.

9. A fragrance composition comprising a compound selected from the class of compounds having the structural formulae

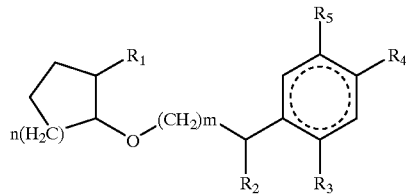

wherein the cyclohexane moiety with the dotted circle represents either a cyclohexane ring or a benzene ring, n represents an integer with the value 1, 3, or 4, m represents an integer with the value 1 or 2, $R_1$, $R_2$, $R_3$, $R_4$, and $R_5$ represent hydrogen or a lower alkyl group, and the total carbon number of $R_1$, $R_2$, $R_3$, $R_4$, and $R_5$ combined is eight or less.

10. A composition according to claim 9 wherein n represents the value 1.

11. A composition according to claim 9 wherein the cyclohexane moiety with the dotted circle represents a benzene ring.

12. A composition according to claim 11 wherein n and m both represent the value 1.

13. A composition according to claim 12 wherein $R_1$, $R_2$, $R_3$, $R_4$, and $R_5$ represent hydrogen.

14. A composition according to claim 9 which further comprises a compound selected from the class of compounds having the structural formulae wherein m represents an integer with the value 1 or 2 and $R_2$, $R_3$, $R_4$, and $R_5$ represent hydrogen or a lower alkyl group, and/or with a compound selected from the class of compounds having the structural formulae

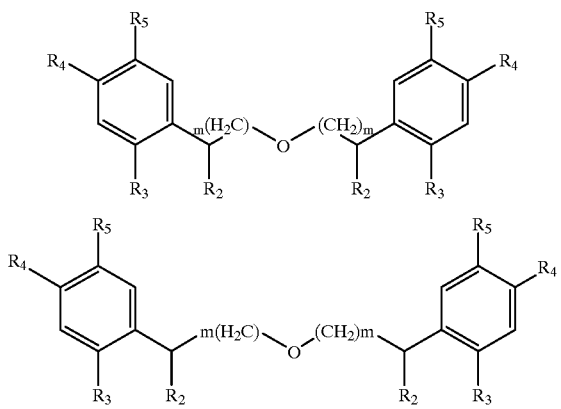

wherein m represents an integer with the value 1 or 2 and $R_2$, $R_3$, $R_4$, and $R_5$ represent hydrogen or a lower alkyl group, provided that the compounds of that mixture have the same definition for m, $R_2$, $R_3$, $R_4$, and $R_5$.

15. A composition according to claim 9 which further comprises at least one other olfactory ingredient.

16. A composition according to claim 9 which is a perfume.

17. A method of producing a desired olefactory effect comprising providing in a product a compound selected from the class of compounds having the structural formulae

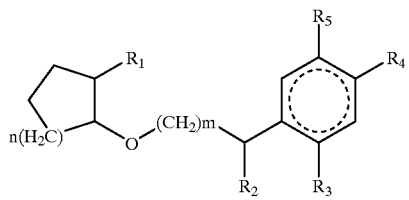

wherein the cyclohexane moiety with the dotted circle represents either a cyclohexane ring or a benzene ring, n represents an integer with the value 1, 3, or 4, m represents an integer with the value 1 or 2, $R_1$, $R_2$, $R_3$, $R_4$, and $R_5$ represent hydrogen or a lower alkyl group, and the total carbon number of $R_1$, $R_2$, $R_3$, $R_4$, and $R_5$ combined is eight or less.

18. A method according to claim 17 wherein n represents the value 1.

19. A method according to claim 17 wherein the cyclohexane moiety with the dotted circle represents a benzene ring.

20. A method according to claim 19 wherein n and m both represent the value 1.

21. A method according to claim 20 wherein $R_1$, $R_2$, $R_3$, $R_4$, and $R_5$ represent hydrogen.

22. A method according to claim 17 which further comprises providing in said product a compound selected from the class of compounds having structural formulae

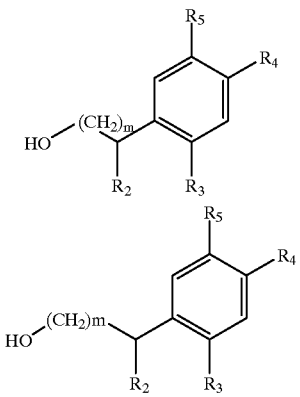

wherein m represents an integer with the value 1 or 2 and $R_2$, $R_3$, $R_4$, and $R_5$ represent hydrogen or a lower alkyl group, and/or with a compound selected from the class of compounds having the structural formulae

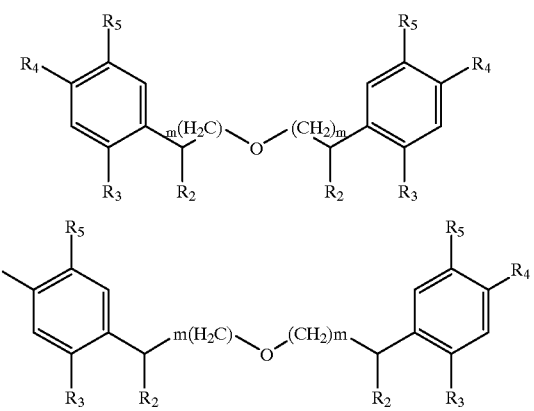

wherein m represents an integer with the value 1 or 2 and $R_2$, $R_3$, $R_4$, and $R_5$ represent hydrogen or a lower alkyl group, provided that the compounds of that mixture have the same definition for m, $R_2$, $R_3$, $R_4$, and $R_5$.

23. A method according to claim 17 which further comprises applying said product to an end use.

24. A method according to claim 23 wherein said product is a perfume which is applied to a perfume wearer.

* * * * *

UNITED STATES PATENT AND TRADEMARK OFFICE
CERTIFICATE OF CORRECTION

| | |
|---|---|
| PATENT NO. | : 6,319,889 B1 |
| APPLICATION NO. | : 09/360306 |
| DATED | : November 20, 2001 |
| INVENTOR(S) | : Lenselink et al. |

It is certified that error appears in the above-identified patent and that said Letters Patent is hereby corrected as shown below:

| | |
|---|---|
| On Title Page, in the Title, | now reads "Chemical Compounds and Perfume Composition" should read --Novel Chemical Compounds and Perfume Composition--; |
| In Column 2, | delete the second structural formula beginning at line 12 and ending at line 18; |
| In Column 2, | delete the second structural formula beginning at line 35 and ending at line 43; |
| In Column 5, line 11, | now reads "with stirring. cyclooctene" should read --with stirring. To this mixture was added 248g cyclooctene-- |
| In Column 7, | delete the second structural formula beginning at line 31 and ending at line 38; |
| In Column 7, | delete the second structural formula beginning at line 53 and ending at line 61; |
| In Column 8, | delete the second structural formula beginning at line 53 and ending at line 61; |
| In Column 9, | delete the second structural formula beginning at line 10 and ending at line 17; |
| In Column 10, | delete the second structural formula beginning at line 13 and ending at line 19; and |

UNITED STATES PATENT AND TRADEMARK OFFICE
CERTIFICATE OF CORRECTION

PATENT NO. : 6,319,889 B1
APPLICATION NO. : 09/360306
DATED : November 20, 2001
INVENTOR(S) : Lenselink et al.

It is certified that error appears in the above-identified patent and that said Letters Patent is hereby corrected as shown below:

In Column 10, delete the second structural formula beginning at line 34 and ending at line 42.

Signed and Sealed this

Third Day of June, 2008

JON W. DUDAS
*Director of the United States Patent and Trademark Office*